United States Patent
Jackson

(10) Patent No.: US 8,257,402 B2
(45) Date of Patent: Sep. 4, 2012

(54) CLOSURE FOR ROD RECEIVING ORTHOPEDIC IMPLANT HAVING LEFT HANDED THREAD REMOVAL

(76) Inventor: Roger P. Jackson, Prairie Village, KS (US)

( * ) Notice: Subject to any disclaimer, the term of this patent is extended or adjusted under 35 U.S.C. 154(b) by 1465 days.

(21) Appl. No.: 10/784,066

(22) Filed: Feb. 20, 2004

(65) Prior Publication Data

US 2004/0167526 A1    Aug. 26, 2004

Related U.S. Application Data

(63) Continuation-in-part of application No. 10/236,123, filed on Sep. 6, 2002, now Pat. No. 6,726,689.

(51) Int. Cl.
*A61B 17/70* (2006.01)
(52) U.S. Cl. .................................. 606/273
(58) Field of Classification Search .............. 606/61, 606/73, 246, 264, 273, 275, 278, 279, 301, 606/305, 308, 315; 411/411, 416
See application file for complete search history.

(56) References Cited

U.S. PATENT DOCUMENTS

| | | |
|---|---|---|
| 791,548 A | 6/1905 | Fischer |
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,295,314 A | 9/1942 | Whitney |
| 2,537,029 A | 8/1946 | Cambern |
| 2,445,978 A | 7/1948 | Stellin |
| 2,532,815 A | 12/1950 | Kindsvatter |
| 2,553,337 A | 5/1951 | Shafer |
| 2,778,265 A | 1/1957 | Brown |
| 2,969,250 A | 1/1959 | Kull |
| 2,877,681 A | 3/1959 | Brown |
| 2,927,332 A | 3/1960 | Moore |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |

(Continued)

FOREIGN PATENT DOCUMENTS

DE    3630863    3/1988

(Continued)

OTHER PUBLICATIONS

Full translation of Shafer (DE 298 10 798 U1), Schreiber Translations, Inc., May 2010 (annotated by Examiner to include page numbers for discussion purposes).*

(Continued)

*Primary Examiner* — Eduardo C Robert
*Assistant Examiner* — David Comstock
(74) *Attorney, Agent, or Firm* — John C. McMahon

(57) ABSTRACT

An anti-splay closure with a left handed threaded removal bore, includes a cylindrical closure body with an external, continuous, helically extending anti-splay guide and advancement flange and a breakaway installation head. The removal bore is aligned with an axis of the closure body. The bore thread is sized and shaped to receive a removal tool having mating left handed thread. The closure is used with an open headed bone implant screw which is provided with internal, helically extending mating guide and advancement structure complementary to the flange of the closure body.

20 Claims, 3 Drawing Sheets

U.S. PATENT DOCUMENTS

| | | |
|---|---|---|
| 3,640,416 A | 2/1972 | Temple |
| 3,812,757 A | 5/1974 | Reiland |
| 3,963,322 A | 6/1976 | Cryctko |
| 4,103,422 A | 8/1978 | Weiss |
| 4,269,246 A | 5/1981 | Larson et al. |
| 4,373,754 A | 2/1983 | Bollfrass et al. |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,703,954 A | 11/1987 | Ortloff et al. |
| 4,707,001 A | 11/1987 | Johnson |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,838,264 A | 6/1989 | Bremer et al. |
| 4,850,775 A | 7/1989 | Lee |
| 4,946,458 A | 8/1990 | Harms et al. |
| 5,005,562 A | 4/1991 | Cotrel |
| 5,022,791 A | 6/1991 | Isler |
| 5,026,373 A | 6/1991 | Ray et al. |
| 5,067,955 A | 11/1991 | Cotrel |
| 5,073,074 A | 12/1991 | Corrigan et al. |
| 5,092,635 A | 3/1992 | DeLange et al. |
| 5,129,388 A | 7/1992 | Vignaud et al. |
| 5,147,360 A | 9/1992 | Dubousset |
| 5,154,719 A | 10/1992 | Cotrel |
| 5,176,483 A | 1/1993 | Baumann et al. |
| 5,207,678 A | 5/1993 | Harms et al. |
| 5,217,497 A | 6/1993 | Mehdian |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,426 A | 3/1997 | Ralph et al. |
| 5,624,442 A | 4/1997 | Mellinger et al. |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,713,705 A | 2/1998 | Grunbichler |
| 5,713,898 A | 2/1998 | Stucker et al. |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,782,833 A | 7/1998 | Haider |
| 5,797,911 A | 8/1998 | Sherman |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,187,005 B1 | 2/2001 | Brace et al. |
| 6,193,719 B1 | 2/2001 | Gournay et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger |
| 6,309,391 B1 | 10/2001 | Crandall et al. |

| Patent | Date | Name |
|---|---|---|
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,932,817 B2 | 8/2005 | Baynham et al. |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,306,606 B2 | 12/2007 | Sasing |
| 2001/0001119 A1 | 5/2001 | Lombardo |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096653 A1 | 5/2005 | Doubler |
| 2005/0107788 A1 | 5/2005 | Beaurain et al. |
| 2005/0113927 A1 | 5/2005 | Malek |

| Pub. No. | Date | Inventor |
|---|---|---|
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Liebermann |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |

FOREIGN PATENT DOCUMENTS

| | | |
|---|---|---|
| DE | 373809 | 5/1989 |
| DE | 19509331 | 9/1995 |
| DE | 4425392 | 11/1995 |
| DE | 19507141 | 9/1996 |
| DE | 29810798 | 12/1999 |
| DE | 19951145 | 5/2001 |
| DE | 10157969 | 2/2003 |
| EP | 195455 | 9/1986 |
| EP | 172130 | 2/1987 |
| EP | 276153 | 7/1988 |
| EP | 0276153 | 7/1988 |
| EP | 465158 | 1/1992 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1277444 | 1/2003 |
| EP | 1449486 | 8/2004 |
| EP | 1570795 | 9/2005 |
| EP | 1579816 | 9/2005 |
| EP | 1634537 | 3/2006 |
| FR | 2467312 | 4/1981 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 203508 | 9/1923 |
| GB | 2082709 | 3/1982 |
| GB | 2140523 | 11/1984 |
| GB | 9202745.8 | 4/1992 |
| GB | 2365345 | 2/2002 |
| JP | 9-504727 | 5/1997 |
| RU | 371359 | 8/1973 |
| SU | 371359 | 2/1993 |
| WO | WO 92/03100 | 5/1992 |
| WO | WO94/10927 | 5/1994 |
| WO | WO94/10944 | 5/1994 |
| WO | WO 9426191 | 11/1994 |
| WO | WO95/35067 | 12/1995 |
| WO | WO96/06576 | 3/1996 |
| WO | WO96/28118 | 9/1996 |
| WO | WO97/14366 | 4/1997 |
| WO | WO98/32386 | 7/1998 |
| WO | WO01/49191 | 7/2001 |
| WO | WO02/054966 | 7/2002 |
| WO | WO03/068088 | 8/2003 |
| WO | WO2004/021900 | 3/2004 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

OTHER PUBLICATIONS

*Spine*, Lipcott, Williams & Wilkins, Inc., vol. 24, No. 15, p. 1495.
Brochure of Tyco/Healthcare/Surgical Dynamics on Spiral Radius 90D, Publication Date: Sep. 2001, pp. 1-8.
CD Horizon M8 Multi Axial Screw Spinal System Brochure, Medtronic Sofamor Danek, no publish date.
EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.

* cited by examiner

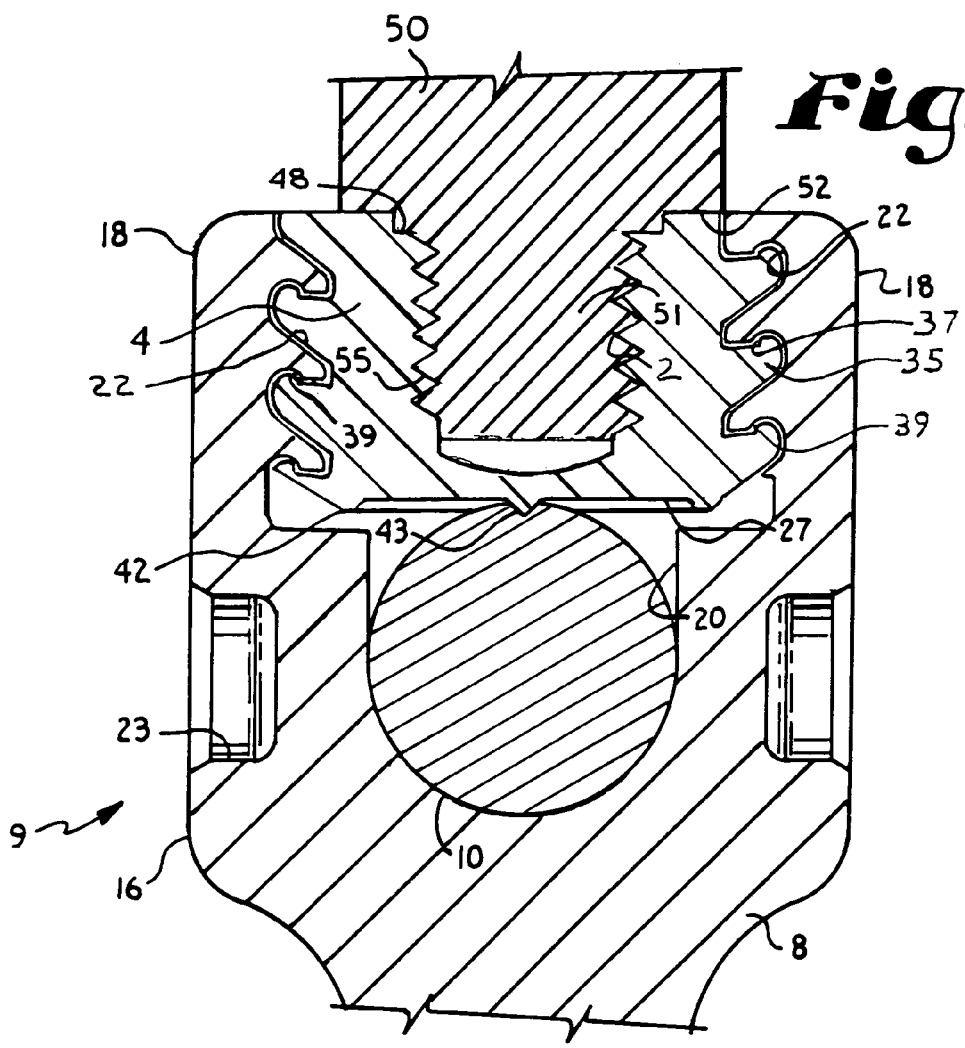
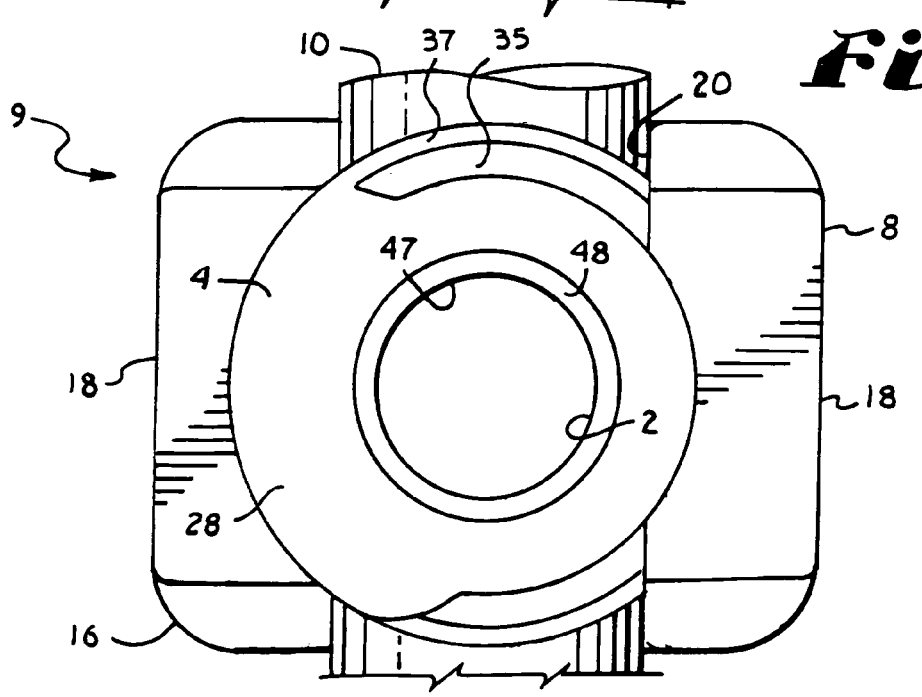

CLOSURE FOR ROD RECEIVING ORTHOPEDIC IMPLANT HAVING LEFT HANDED THREAD REMOVAL

CROSS-REFERENCE TO RELATED APPLICATION

This is a continuation-in-part of U.S. patent application, Ser. No. 10/236,123 filed Sep. 6, 2002 for HELICAL WOUND MECHANICALLY INTERLOCKING MATING GUIDE AND ADVANCEMENT STRUCTURE, which is now U.S. Pat. No. 6,726,689.

BACKGROUND OF THE INVENTION

The present invention is directed to a closure for operably securing a rod to an orthopedic implant wherein said closure includes a break off head, a left hand threaded axially aligned bore for use in removal of the closure from the implant and a structure for use in interlocking together the closure and the implant. The interlocking structure includes a first interlocking form on the closure and a mating second interlocking form on the implant. The closure is operably rotated into the implant and against the rod for securing the rod in the implant. The first and second interlocking forms are both helically wound so that the first interlocking form advances relative to the second interlocking form and toward the rod, when the closure with the first interlocking form is inserted in the implant and rotated. At least one of the first or second interlocking forms includes a projection that overlaps and radially locks with the other interlocking form, when the two forms are mated.

Medical implants present a number of problems to both surgeons installing the implants and to engineers designing them. It is always desirable to have an implant that is strong and unlikely to fail or break during usage. It is also desirable for the implant to be as small and lightweight as possible so that it is less intrusive on the patient. These are normally conflicting goals and often difficult to resolve.

One particular type of implant presents special problems. In particular, spinal bone screws, hooks, etc. are used in many types of back surgery for repair of injury, disease or congenital defect. For example, spinal bone screws of this type are designed to have one end that inserts threadably into a vertebra and a head at an opposite end thereof. The head is designed to receive a rod or rod-like member in a channel in the head. The rod is then both captured in the channel and locked in the head to prevent relative movement between the various elements subsequent to installation.

There are two different major types of bone screws and similar devices which are classified as closed headed and open headed. While the closed headed devices are highly effective at capturing and securing a rod, it is very difficult during surgery to insert the rod through the heads, since the rod must be introduced through an opening in the head. This is because there are many bone screw heads used and the rod is often curved or the heads do not align. Consequently, the more screw heads that the rod must pass through, the more difficult it is to manipulate the rod into and through them.

The second type of head is an open head wherein a channel is formed in the head and the rod is simply laid in an open channel. The channel is then closed with a closure member. The open headed bone screws and related devices are much easier to use and in some situations must be used instead of the closed headed devices.

While the open headed devices are often necessary and often preferred for usage, there is a significant problem associated with them. In particular, the open headed devices conventionally have two upstanding arms that are on opposite sides of a channel that receives the rod member. The top of the channel is closed by a closure member after the rod member is placed in the channel. Forces applied during installation or during accidents can cause the arms to splay or spread at the top which may result in failure of the implant if the arms splay sufficiently to loosen or release the closure. The closure can be of a slide in type, but such are not easy to use. Threaded nuts are sometimes used that go around the outside of the arms. Such nuts prevent splaying of the arms, but nuts substantially increase the size and profile of the implant which is not desirable. Many open headed implants are closed by plugs that screw into threads between the arms, because such have a low profile. However, threaded plugs have encountered problems also in that they especially produce forces that are radially outward directed and that lead to splaying or spreading of the arms or at least do not prevent splaying due to other causes that in turn loosens or completely releases the rod relative to the implant. In particular, in order to lock the rod member in place, a significant force must be exerted on the relatively small plug or screw. The forces are required to provide enough torque to insure that the rod member is clamped or locked in place relative to the bone screw, so that the rod does not move axially or rotationally therein. This typically requires torques on the order of 100 inch-pounds.

Because open headed implants such as bone screws, hooks and the like are relatively small, the arms that extend upwardly at the head can be easily bent by radially outward directed forces due to the application of substantial forces required to lock the rod member. Historically, early closures were simple plugs that were threaded with V-shaped threads and which screwed into mating threads on the inside of each of the arms. But, as noted above, conventional V-shaped threaded plugs exert radially outward forces and tend to splay or push the upper ends of the arms radially outward upon the application of a significant amount of torque, which ends up bending the arms relative to a body sufficiently to allow the threads to loosen or disengage from each other and the closure to loosen and/or disengage from the implant and thereby fail. To counter splaying, various engineering techniques were applied to allow the head to resist the spreading force. For example, in one attempt, the arms were significantly strengthened by increasing the width of the arms a significant amount. This had the unfortunate effect of substantially increasing the weight and the profile of the implant, which was undesirable.

Many prior art devices have also attempted to provide outside rings or some other type of structure that goes about the outside of the arms to better hold the arms in place either independently or while a center plug was installed and thereafter. This additional structure may cause the locking strength of the plug against the rod to be reduced which is undesirable, especially when additional structure is partly located between the plug and the rod, as is the case in some devices. Also, the additional elements are unfavorable from a point of view of implants, since it is typically desirable to maintain the number of parts associated with the implants at a minimum and, as noted above, to keep the profile, bulk and weight as minimal as possible.

Prior designers have also attempted to resolve the splaying problem by providing a closure with a pair of opposed radially extending wedges or flanges that are designed to twist ninety degrees and that have mating structure in the arms of the implant. Such devices serve as a closure and do somewhat resist splaying of the arms, but are often very difficult to use. In particular, the rods normally have some curvature as the rods are bent to follow the curvature of the spine and normally bow relative to the bottom of the bone screw channel that receives such a rod. The rod thus fills much of the channel and must be "unbent" to rest on the bottom of the channel or pushed toward the bottom of the channel and held securely in place. Therefore, the rod is preferably compressed and set by the plug by advancement of the plug into the channel in order to assure that the plug will securely hold the rod and that the rod and plug will not loosen when post assembly forces are placed on the rod. Because it takes substantial force to seat the rod, it is difficult to both place the plug fully in the channel and rotate the plug for locking while also trying to line up wedges on the plug with the mating structure. It is much easier to align the closure plug or mating structure with the mating structure of the arms at the top of the arms and then rotate the plug so as to advance the plug in a plug receiver toward the rod. In this way, the plug starts applying significant force against the rod only after parts of the mating structure have at least partly joined at which time torque can be applied without having to worry about alignment. It is also noted that in prior art plugs where wedges are used, the cross section of the structure changes therealong so that the device "locks up" and cannot turn further after only a small amount of turning, normally ninety degrees.

Consequently, a lightweight and low profile closure plug is desired that resists splaying or spreading of the arms while not requiring significant increases in the size of the screw or plug heads and not requiring additional elements that encircle the arms to hold the arms in place.

It is noted that the tendency of the open headed bone screw to splay is a result of the geometry or contour of the threads typically employed in such devices and the inability of threads to timely interlock with each other or a mating structure. In the past, most bone screw head receptacles and screw plugs have employed V-shaped threads. V-threads have leading and trailing sides oriented at angles to the screw axis. Thus, torque on the plug is translated to the bone screw head at least partially in an axial direction, tending to push or splay the arms of the bone screw head outward in a radial direction. This in turn spreads the arms of an internally threaded receptacle away from the thread axis so as to loosen the plug in the receptacle.

The radial expansion problem of V-threads has been recognized in various types of threaded joints. To overcome this problem, so-called "buttress" threadforms were developed. In a buttress thread, the trailing or thrust surface is oriented perpendicular to the thread axis, while the leading or clearance surface remains angled. This theoretically results in a neutral radial reaction of a threaded receptacle to torque on the threaded member received.

Development of threadforms proceeded from buttress threadforms which in theory have a neutral radial effect on the screw receptacle to reverse angled threadforms which theoretically positively draw the threads of the receptacle radially inward toward the thread axis when the plug is torqued. In a reverse angle threadform, the trailing side of the external thread is angled toward the thread axis instead of away from the thread axis, as in conventional V-threads. While buttress and reverse threadforms reduce the tendency to splay, the trailing and leading surfaces of such a threadform are linear allowing opposing sides to slide relative to the surfaces so that the arms can still be bent outward by forces acting on the implant and the threads can be bent by forces exerted during installation. Therefore, while certain threadforms may not exert substantial radial forces during installation, at most such threadforms provide an interference or frictional fit and do not positively lock the arms in place relative to the closure plug.

It is also noted that plugs of this type that use threadforms are often cross threaded. That is, as the surgeon tries to start the threaded plug into the threaded receiver, the thread on the plug is inadvertently started in the wrong turn or pass of the thread on the receiver. This problem especially occurs because the parts are very small and hard to handle. When cross threading occurs, the plug will often screw partially into the receiver and then "lock up" so that the surgeon is led to believe that the plug is properly set. However, the rod is not tight and the implant fails to function properly. Therefore, it is also desirable to have a closure that resists crossthreading in the receiver.

For closures of the type described herein to function properly, such closures are "set" or torqued to a preferred torque, often 95 to 100 inch pounds. The operating region where the implants are installed is within the body and the parts are relatively very small. Consequently, the closures of the present invention preferably can be readily gripped and torqued. In order to reduce profile, a driving or installation head is designed to break away at a preselected torque.

After the closure is installed, it is sometimes necessary to remove the closure. For purposes of removal, the driving head is no longer available, so structure is required to allow quick easy removal and which cooperates effectively with the guide and advancement structure utilized with the closure.

SUMMARY OF THE INVENTION

A non threaded guide and advancement structure is provided for securing a plug or closure in a receiver in an orthopedic implant. The receiver is a rod receiving channel in an open headed bone screw, hook or other medical implant wherein the channel has an open top and is located between two spaced arms of the implant.

The guide and advancement structure has a first part or interlocking form located on the closure and a second part or interlocking form that is located on the interior of the receiving channel. The interlocking forms lock and resist sidewise or radial movement of load bearing leading or trailing surfaces rather than simply interfere with movement due to placement.

Both parts of the guide and advancement structure are spirally or more preferably helically wound and extend about the closure and receiving channel for at least one complete 360° pass or turn. Preferably, both parts include multiple turns such as 2 to 4 complete 360° rotations about the helixes formed by the parts. The helixes formed by the parts are coaxial with the closure when the closure is fully received in or being rotated into the receiving channel between the arms.

One major distinguishing feature of the guide and advancement structure is that each of the parts include elements that mechanically interlock with the opposite part or mating piece as the closure is rotated and thereby advanced into the receiving channel toward the bottom of the channel and into engagement with a rod received in the channel.

Each part of the guide and advancement structure preferably has a generally constant and uniform cross section, when viewed in any cross sectional plane fully passing through the axis of rotation of the closure during insertion, with such uniform cross section preferably extending along substantially the entire length of the interlocking form. Opposite ends of each interlocking form are feathered or the like so the cross section does change some at such locations, while retaining part of the overall shape. In particular, the outer surfaces of each interlocking form remain sufficiently uniform to allow interlocking forms to be rotated together and slide tangentially with respect to each other through one or more complete turns of the closure relative to the receiving channel. Each part may be continuous from near a bottom of the closure or receiving channel to the top thereof respectively. In certain circumstances one or both parts may be partly discontinuous, while retaining an overall helical configuration with a generally uniform cross sectional shape. When the interlocking form has multiple sections dues to being discontinuous, each of the sections has a substantially uniform cross section along substantially the entire length thereof.

In order to provide an interlocking structure, the parts of the structure include helical wound projections or interlocking forms that extend radially outward from the closure and radially inward from the receiving channel. The interlocking forms may be of many different shapes when viewed in cross-section with respect to a plane passing through the axis of rotation of the plug during insertion. In general, the interlocking forms increase in axial aligned width or have a depression at a location spaced radially outward from where the interlocking form attaches to a respective closure or receiving channel, either upward (that is, parallel to the axis of rotation of the closure in the direction from which the closure comes or initially starts) or downward or in both directions. This produces a first mating element that is in the form of a protrusion, bump, ridge, elevation or depression on the interlocking form that has a gripping or overlapping portion. The opposite interlocking form has a second mating element with a gripping or overlapping portion that generally surrounds or passes around at least part of the first mating element in such a way that the two are radially or sideways mechanically locked together when the closure is advanced into the receiving channel.

Therefore, in accordance with the invention a mating and advancement structure is provided for joining two devices, that are preferably medical implants and especially are an open headed implant that includes a rod receiving channel and a closure for closing the receiving channel after the rod is received therein. The mating and advancement structure includes a pair of mateable and helical wound interlocking forms with a first interlocking form located on an outer surface of the closure and a second interlocking form located on an inner surface of the receiving channel or receiver. The first and second interlocking forms are startable so as to mate and thereafter rotatable relative to each other about a common axis so as to provide for advancement of the closure into the receiver during assembly when the closure interlocking form is rotated into the receiver interlocking form. The first and second interlocking forms have a helical wound projection that extends radially from the closure and the receiver respectively. Each interlocking form projection has a base that is attached to the closure or receiver respectively and preferably includes multiple turns that may each be continuous or partially discontinuous with constant or uniform cross-sectional shape. The interlocking forms have substantial axial width near an outer end thereof that prevents or resists misalignment of the interlocking form during initial engagement and rotation thereof.

After assembly, in some embodiments each turn of each projection generally snugly engages turns of the other projection on either side thereof. In other embodiments there must be sufficient tolerances for the parts to slide tangentially, so that when thrust surfaces of the interlocking forms are very close during tightening, some gap occurs on the leading side of the closure interlocking form. In such a case the portions of the interlocking forms on the thrust side thereof lock together and prevent radial splaying.

Located radially spaced from where the base of each projection is attached to either the closure or receiver respectively, is an axially extending (that is extending in the direction of the axis of rotation of the plug or vertically) extension or depression. The opposite or mating interlocking form has elements that wrap around or into such extensions or depressions of the other interlocking form. That is, the forms axially interdigitate with each other and block radial outward movement or expansion. In this way and in combination with the interlocking forms preferably being snug or close relative to each other with sufficient clearance to allow rotation, the interlocking forms, once assembled or mated lock to prevent radial or sideways slipping or sliding relative to each other, even if forces are applied that would otherwise bend the base of one or both relative to the device upon which it is mounted. It is possible that the cross section of the projection (in a plane that passes through the plug axis of rotation of the closure) of each section of each turn or pass of the interlocking form be the same, although this is not required in all embodiments. For example, part of the interlocking form may be missing in the region between opposed arms when assembly is complete as this area is not required to hold the arms together.

Preferably, the present invention provides such an interlocking form for use in a medical implant closure which resists splaying tendencies of arms of a receiver. The interlocking form of the present invention preferably provides a compound or "non-linear" surface on a trailing face, thrust face or flank of the interlocking form, although the "non-linear" surface may also be placed on the leading face.

Preferably, the interlocking form located on the closure is helically wound about a cylindrical outer surface of the closure and has an inner root, and an outer crest that remain constant over substantially the entire length of the interlocking form. The receiver has a mating or similar shaped interlocking form wound about the interior thereof. In this embodiment the interlocking form has leading or clearance surfaces and trailing or thrust surfaces, referenced to the direction of axial movement of the form when rotated into one another. The structure also includes an internal helical wound interlocking form located on an internal surface of a receiver member and has an outer root and an inner crest. The internal interlocking form has thrust surfaces which are oriented in such a direction so as to be engaged by the thrust surfaces of the external interlocking form of a member engaged therewith.

In certain embodiments, the thrust surfaces are "non-linear" or compound. That is, the thrust surfaces have a non-linear appearance when represented in cross section. The purpose for the non-linear or compound surface is to provide a portion of the thrust surface which is oriented in such a direction so as to resist a tendency of the receiver to expand or splay when tightening torque is applied to rotate the interlocking forms into a mating relationship or when other forces are encountered. As applied to a closure for an open headed bone implant screw, the non-linear or compound surfaces of the interlocking forms whether on tracking surfaces, leading surfaces or both interlock and resist splaying tendencies of the arms of the head. The objective of the interlocking form is not necessarily to generate a radially inwardly directed force on the receptacle in tightening the fastener (although this may occur in some embodiments), but importantly to resist outward forces generated by engagement of the closure with the closure receptacle or by other forces applied to the components joined by the closure and closure receptacle and prevent splaying. It is noted that the present invention requires that only a portion of the thrust surfaces of a closure be so configured as to face toward the closure axis and only a portion of thrust surfaces of a closure receptacle face away from the axis.

In certain embodiments, an axial extension or depression is located on the thrust or trailing surface, or alternatively for such to be located on the opposite or leading surface or both.

Further, in some embodiments a section of the interlocking form at the crest, that is located radially outward of the root, is enlarged in cross sectional area to create a gripping, locking or stopping surface that resists slippage or sliding in a radial direction relative to an opposed interlocking form. In a complementary manner, a section of the interlocking form between the root and the crest which is radially spaced from the root is enlarged in cross sectional area to create a gripping, locking or stopping surface that engages a like surface of the opposite interlocking form. The enlarged sections of the inner and outer interlocking forms are created by cutting, molding, machining or the like grooves or channels or the like into a radially inward portion of the thrust surface of the external interlocking form and mating grooves or channels into a radially outward portion of the thrust surface of the internal interlocking form. Such grooves or channels may be formed by specially shaped taps and dies, cutting elements or by other suitable manufacturing processes and technologies, including molding.

The interlocking forms of the present invention may be implemented in a variety of configurations of non-linear, compound, or complex trailing and/or leading surfaces. The nomenclature used to describe variations in the interlocking forms of the present invention is especially referenced to the external interlocking forms located on a closure, with complementary, mating or similar shapes applied to the internal interlocking forms on a receiver. In an axial shoulder interlocking form of the present invention, a somewhat squared gripping shoulder is formed near an outer periphery of the external interlocking forms and an inner gripping surface on the internal interlocking forms. The axial shoulder interlocking form results in complementary cylindrical surfaces on the external and internal interlocking forms which mutually engage when the fastener or closure is rotated into a closure receptacle.

In an axial extending bead interlocking form, the external interlocking form is provided with a rounded peripheral bead or lateral lip which projects in an axial direction along the interlocking form crest and a complementary rounded concave channel in the internal interlocking form. The reverse occurs with the internal interlocking form.

Other alternative forms include a radial bead interlocking form wherein a rounded bead enlargement is formed on the radially outward periphery at the crest of the external interlocking form, while the internal interlocking form is formed in a complementary manner to receive the radial bead interlocking form. A scalloped or scooped interlocking form which is, in effect, a reciprocal of the axial bead interlocking form and has a rounded channel or groove located along the thrust surface of the external interlocking form with a complementary rounded convex bead shape associated with the internal interlocking form. A variation of the axial bead interlocking form is a medial bead embodiment. In the medial bead interlocking form, a bead projects from a base thrust surface of an external interlocking form in an axial direction at a location medially between the root and crest of the interlocking form. In a complementary medial bead internal interlocking form, an axial groove is formed in a base thrust surface between the root and crest. In a medial groove interlocking form, an axial groove is formed in a base thrust surface of the external interlocking form medially between the root and crest, while the internal interlocking form has an axial bead located medially between the root and crest.

Variations in the above described interlocking forms are envisioned with respect to relative extensions or enlargements and depressions or depth of grooves of the various interlocking forms. In some variations, the opposite interlocking forms have the same but reversed and inverted cross section, whereas in others the cross section of the paired interlocking forms mates but is different. It is noted that many other configurations of interlocking forms with non-linear, compound or complex thrust surfaces are envisioned, which would be encompassed by the present invention.

The interlocking forms of the present invention find particularly advantageous application in various types of bone implant devices. The interlocking forms also have advantages in reducing misalignment problems of cross-interlocking and misinterlocking of interlocking forms when the opposed interlocking forms are joined and rotated which is commonly encountered in such devices when threads of various types are used.

A breakoff head is provided for rotating and driving the closure along the axis of the receiver. The breakoff head is axially secured to the closure and breaks from the remainder of the closure after the closure is set against a rod and a predetermined torque is obtained, for example 100 inch pounds.

Axially penetrating the closure from the top thereof and being fully exposed by the breakoff head being broken therefrom is a bore. The bore may be fully penetrating or partially penetrating from top to bottom of the closure. The bore has an interior left handed thread that is sized and shaped to receive a like threaded tool that can be rotated counterclockwise after insertion to also rotate the closure body counterclockwise to remove the body should removal be required after installation.

OBJECTS AND ADVANTAGES OF THE INVENTION

Therefore, objects of the present invention include providing an improved closure plug or closure top for use with an open headed bone screw; providing such a closure having a cylindrical base and a driving or installation head that breaks away from the base at a breakaway region to provide a low or minimized profile subsequent to installation of the closure; providing such a closure having removal structure enabling positive, non-slip engagement of the closure by a removal tool which securely grips and holds the closure; providing such a closure having an axially extending bore that passes through the installation head and at least into the closure; providing such a closure in which the bore has an internal left handed thread that is sized and shaped to receive a removal tool with a matingly threaded projection; providing such a closure in combination with an open headed bone implant screw for use in anchoring a bone fixation structural member, such as a rod; providing such a closure combination in which the open headed bone screw includes a pair of spaced apart arms forming a rod receiving channel; providing such a closure combination including an external guide and advancement flange on the closure and mating internal guide and mating structure on inner surfaces of the bone screw head which interlock and cooperate to resist tendencies of the arms to splay or diverge when the closure is torqued tightly into clamping engagement with a rod positioned in the channel or when outside forces are applied to the structure; providing such a combination including features to enhance setting engagement of the closure with a rod in the bone screw channel; providing such a combination in which a forward end of the closure is provided with a peripheral cutting cup or V-ring and point to cut into the surface of the rod when the closure is securely torqued, to resist translational and rotational movement of the rod relative to the bone screw; and providing such an anti-splay closure plug or fastener which is economical to manufacture, which is secure and efficient in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

BRIEF DESCRIPTION OF THE DRAWINGS

FIG. 8 is an enlarged top plan view of the closure within the open headed bone screw subsequent to breaking away of the break off head.

FIG. 9 is an enlarged cross sectional view of the closure of the present invention, taken along the line 5-5 of FIG. 3 but subsequent to installation in the bone screw and illustrates details of anti-splay structure of the closure and bone screw head, further illustrating a removal tool inserted in the bore for effecting removal of the closure from the bone screw.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
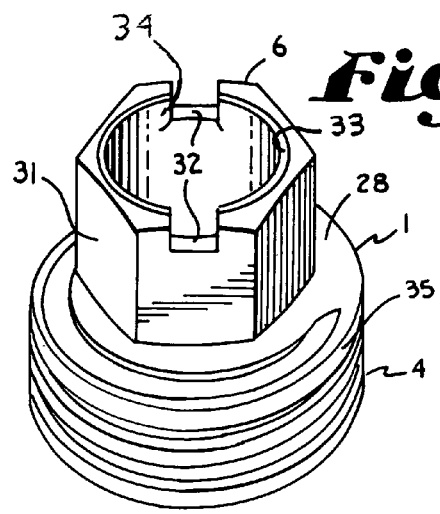
FIG. 1 is an enlarged perspective view of an anti-splay closure with a break off driving head in accordance with the present invention.
Figure 2:
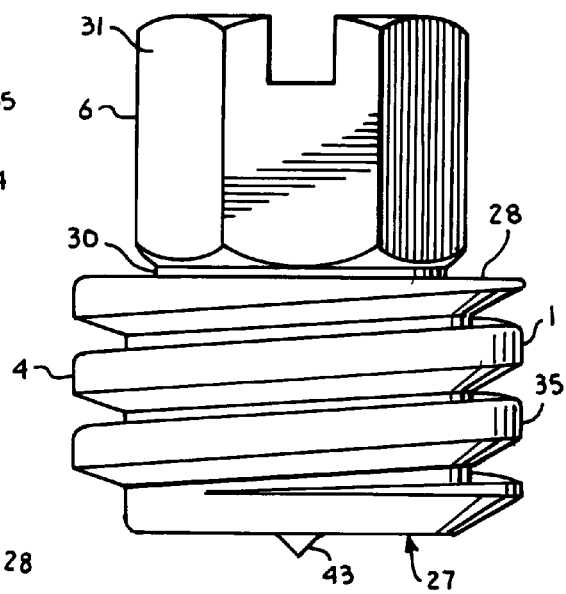
FIG. 2 is a side elevational view of the closure at a further enlarged scale.
Figure 3:
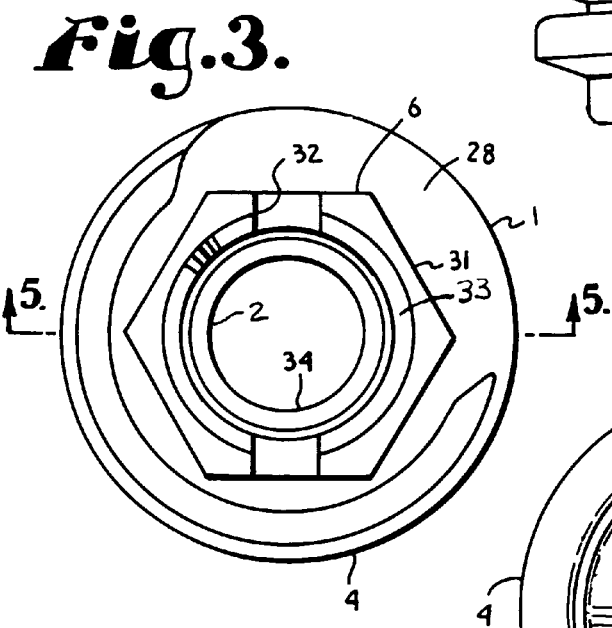
FIG. 3 is a top plan view of the closure.
Figure 4:
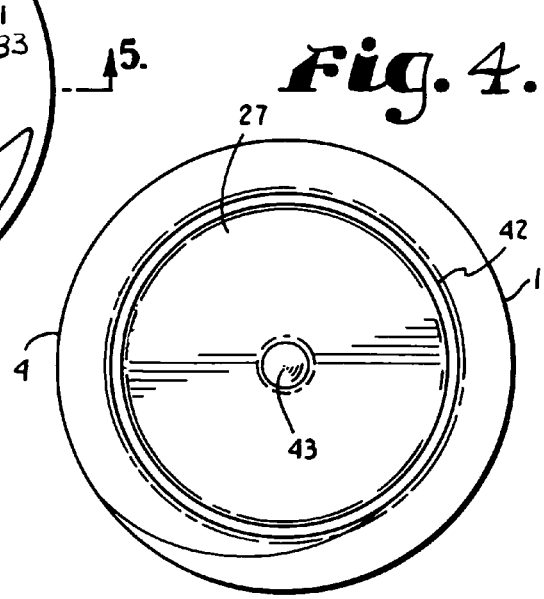
FIG. 4 is a bottom plan view of the closure that illustrates a V-ring and point on the bottom of the closure.
Figure 5:
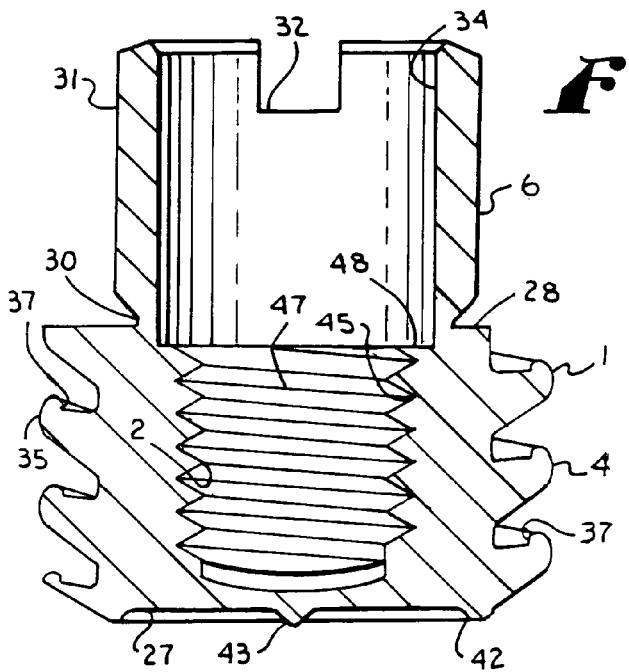
FIG. 5 is a cross sectional view of the closure, taken on line 5-5 of FIG. 3 and illustrates internal details of the break off head and an internal threaded bore.
Figure 6:
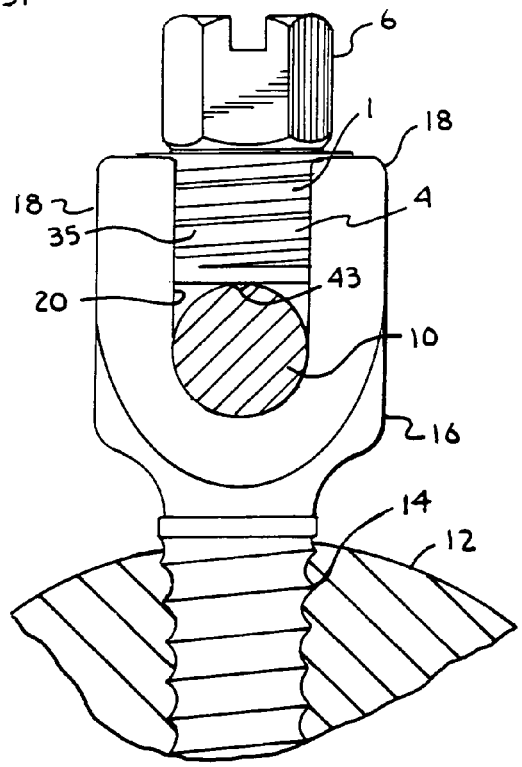
FIG. 6 is a fragmentary side elevational view at a reduced scale of the closure in combination with an open headed bone screw implant, prior to separation of the break off head.

Referring to the drawings in more detail, the reference numeral 1 generally designates an anti-splay closure with a partial axial bore 2. The closure 1 generally includes a closure plug or body 4 and a breakaway head 6 for installation. The closure 4 is used in cooperation with an open headed bone implant screw 8 (FIGS. 6 and 7) to form an implant anchor assembly 9 to secure or anchor a spinal fixation member or rod 10 with respect to a bone 12, such as a vertebra.

The bone screw 8 includes a threaded shank 14 for threadably implanting the screw 8 into the bone 12 and an open head 16 having a pair of upwardly extending and spaced apart arms 18 defining a U-shaped channel 20 therebetween to receive the rod 10. Inner surfaces of the arms 18 have an internal guide and advancement structure 22 (FIG. 9) tapped, or otherwise formed, therein. The head 16 includes grip indentations 23 (FIG. 9) to facilitate gripping the bone screw 8 by an appropriate screw gripping tool (not shown) during manipulation for implantation of the bone screw 8 into the bone 12.

Figure 7:
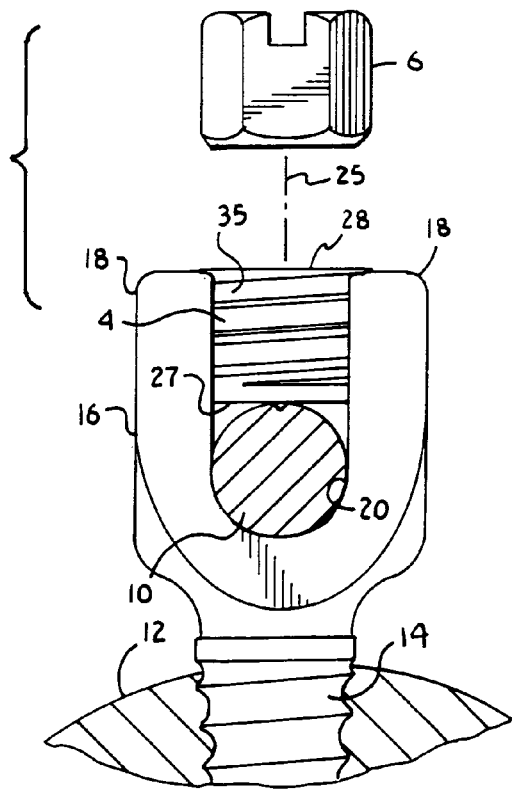
FIG. 7 is a view similar to FIG. 6 and illustrates separation of the break off head of the closure due to exceeding a preselected torque thereon.

The closure body 4 is cylindrical in external shape about a closure axis 25 (FIG. 7) and has a forward, leading, or inner end 27 on the bottom and a rear, trailing, or outer end 28 on the top. The breakaway or breakoff head 6 is connected to the body 4 at the rear end 28 by way of a weakened region represented by a breakaway line or ring 30 formed by selectively reducing the wall thickness of the closure 1 in that region so as to weaken the region. The breakaway ring 30 is thinned in such a manner that it fails when a preselected torque is applied to the body 4, as a result of torque being applied to the head 6 by conventional socket tools or the like to rotate and tighten the body 4 within the bone screw 8. As illustrated, the break off head 6 has a hexagonal outer surface 31 to facilitate non-slip engagement by an installation tool (not shown). The head 6 may also be provided with a set of tool slots 32 for alternative or more positive non-slip engagement of the head 6 by the installation tool. The head 6 has a central and axially aligned bore 34 that is coaxial with the removal bore 2 and that defines the break off point of the head 6 in conjunction with the ring 30 and ends in a chamfer 33. Separation of the head 6 from the body 4, as shown in FIG. 7, is desirable to control or limit torque applied by the body 4 to the rod 10 within the bone screw head 16, preferably such that the body 4 is at or below the tops of the arms 18 so as to present a low profile.

The body 4 is provided with a guide and advancement flange 35 which coaxially extends helically about the cylindrical body 4. The flange 35 is enlarged at its outer periphery or radial crest to form a generally inwardly facing or inward anti-splay surface 37. In a similar manner, the bone screw guide and advancement structures 22 which are discontinuous but which matingly engage and receive the body flange 35 are enlarged at their radially outward peripheries or roots to form generally outwardly facing or outward anti-splay surfaces 39. The anti-splay or splay resisting surfaces 37 and 39 face each other and mutually engage when the body 4 is advanced into the bone screw head 16 and particularly when the body 4 is strongly torqued within the head 16 to resist any tendency of the arms 18 to be urged outwardly, or splayed, in reaction to such torque.

Although particular contours of the flange 35 and mating structure 22 are shown herein, other contours of anti-splay guide and advancement flanges and mating structure are foreseen. Examples of such alternative configurations of anti-splay or splay resisting guide and advancement flange and mating structures are disclosed in U.S. patent application, Ser. No. 10/236,123 which is now U.S. Pat. No. 6,726,689, which is incorporated herein by reference. The flange 35 and mating structures 22 cooperate to guide and advance the body 4 into clamping engagement with the rod 10 within the channel 20 in response to rotation of the closure 1.

In order to more positively secure the rod 10 within the head 16 of the bone screw 8, the closure 4 is provided with penetrating structure such as a V-ring 42 and an axially aligned point 43 on the inner or forward end 27 thereof. The V-ring 42 cuts into the surface of the rod 10 when the body 4 is tightly torqued into the head 16. The V-ring 42 extends about a periphery of the inner end 27 of the body 4 and, thus, provides two possible areas of engagement between the body 4 and the rod 10, particularly if the rod 10 is relatively straight and acts with the point 43 to help secure the rod 10 in the bone screw 8.

In the great majority of cases, the body 4 is torqued into engagement with the rod 10 in the bone screw 8, the installation head 6 is broken away, and the anchor assembly 9 is permanently implanted in the bone 12. However, spinal alignment geometry is complex, and it is sometimes necessary to make adjustments to a spinal fixation system. Additionally, slippage or failure of spinal fixation components can occur due to injury to the patient, deterioration of bone tissue, or the like. It is also possible that an implant system using anchored rods might be used therapeutically, for example, to set a broken bone, and subsequently removed. For these reasons, implant anchor assemblies require a structure or mechanism for removing an anchor assembly 9 to make such adjustments or changes in the spinal fixation system. The anchor assembly 9 of the present invention allows retraction and removal of the closure body 4 from the bone screw head 16 to release the rod 10 to allow repositioning of the rod 10 relative to the bone screw 8 or overall removal of the bone screw 8 and rod 10.

The body 4 includes the bore 2 which extends from the outer surface 28 axially partially therethrough. The bore 2 has an inner cylindrical surface 45 that has a left handed thread 47 thereon. The bore surface 45 has a short shoulder 48 whereat it engages the top of the body 4 that becomes part of the outer surface 28 when the head 6 breaks from the body 4.

The body 4 is removed from the screw 8 by placement of a tool 50 (see FIG. 9) having a projection 51 that is joined to a remainder of the tool 50 by a shoulder 53. The projection 51 has thereon a left handed thread 55 that is sized and shaped to mate with the bore thread 47. The tool 50 includes a handle (not shown) or the like to provide for rotation. When the tool 50 is screwed counterclockwise into and implanted in the body 4, as shown in FIG. 9, and thereafter further rotated counterclockwise, the body 4 rotates counterclockwise and moves in an axial and upward direction (as seen in FIG. 9), so that the body 4 is removed from the bone screw head 16 and securely held.

Although a particular fixed headed bone screw is shown herein, it is foreseen that the present invention may be utilized with other types of implants, including polyaxial head bone screws of all types, hooks and other implants wherein a channel receives a rod or rodlike member and the rod requires securing against movement relative to the bone screw or other implant.

It is to be understood that while certain forms of the present invention have been illustrated and described herein, it is not to be limited to the specific forms or arrangement of parts described and shown.

What is claimed and desired to be secured by Letters Patent is as follows:

1. A closure for setting engagement with a structural member and comprising:
   (a) a substantially cylindrical body having an outer cylindrical surface relative to a central closure axis;
   (b) a guide and advancement flange extending helically about said outer cylindrical surface and having a forward advancement direction relative to said closure axis, said flange having a leading surface and a trailing surface relative to said forward advancement direction;
   (c) said trailing surface being compound in contour and including an inward substantially horizontal surface and an outer raised portion; the leading surface sloping outwardly rearwardly;
   (d) a driving structure for rotating and torquing said body to a preselected torque; and
   (e) said body having an axially aligned bore opening on a trailing surface of said body; said bore having a left handed thread that includes a plurality of complete revolutions of the thread about the bore therein that is sized and shaped to be adapted to receive a removal tool with a mating left handed thread for removing said body subsequent to installation.

2. The closure as set forth in claim 1 wherein said bore is exposed by removal of said driving structure.

3. The closure as set forth in claim 1 wherein:
   (a) said apertures extend from said body trailing surface partially therethrough.

4. The closure as set forth in claim 1 wherein:
   (a) said driving structure is an installation head that includes a grippable radially outer surface that is shaped to enable non-slip engagement of said installation head by an installation tool; and
   (b) said installation head being connected to said closure by a breakaway region formed in such a manner that said breakaway region fails in response to a selected level of torque between said installation head and said closure to enable separation of said installation head from said closure.

5. The closure as set forth in claim 1 and including:
   (a) said closure having a leading surface relative to said forward advancement direction; and
   (b) said body having a V-shaped set ring and an axially aligned point formed on said leading end to enhance setting engagement of said closure into a surface of a structural member.

6. The closure as set forth in claim 1 in combination with a bone implant screw adapted for connection to a bone fixation structural member, said bone implant screw including:
   (a) a threaded shank adapted for threaded implanting into a bone;
   (b) an open head formed by a pair of spaced apart arms having mutually facing channel surfaces defining a structural member receiving channel therebetween to receive a bone fixation structural member; and
   (c) said mutually facing channel surfaces each having mating guide and advancement structure formed therein which are compatible for mating with said guide and advancement flange of said closure to enable rotation guiding and advancement of said closure into said channel so as to be adapted to clamp said bone fixation structural member when positioned therein.

7. The closure and bone implant screw combination as set forth in claim 6 wherein:
   (a) said mating guide and advancement structure of said bone implant screw include an outward anti-splay surface component which cooperates with said inward anti-splay surface component of said closure to provide an interlocking fit when joined so as to resist splaying of said arms in reaction to forces applied thereto.

8. The closure and bone screw combination as set forth in claim 7 wherein:
   (a) said guide and advancement flange has a relatively enlarged outer periphery which forms said inward anti-splay surface component;
   (b) said mating guide and advancement structures are contoured in a complementary manner to said guide and advancement flange to form said outward anti-splay surface component; and
   (c) said inward anti-splay surface component engages said outward anti-splay surface component when said closure is guided and advanced into said open screw head of said bone implant screw.

9. A closure for setting engagement with a bone screw and comprising:
 (a) a body having an outer cylindrical surface relative to a central closure axis and a driving installation head;
 (b) a guide and advancement flange extending helically and substantially continuously about said outer cylindrical surface and having a forward advancement direction relative to said closure axis, said flange having a trailing surface relative to said forward advancement direction;
 (c) said trailing surface being compound in contour and including an inward radial loading surface and an outward raised portion with a top surface that remains unloaded when in a locked position; said leading surface sloping outwardly rearwardly and being free of any engagement with an opposed surface of the bone screw; and
 (d) said body having an axially aligned bore formed therein that opens onto a trailing surface of said body; said bore having a helically wound left handed thread therein that extends a plurality of revolutions about the bore; said bore thread being sized and shaped to receive a removal tool having a mating left handed thread.

10. The closure as set forth in claim 9 including:
 (a) an installation head that is shaped to enable non-slip engagement of said installation head by an installation tool; and
 (b) said installation head being connected to said closure by a breakaway region formed in such a manner that said breakaway region fails in response to a selected level of torque between said installation head and said closure to enable separation of said installation head from said closure.

11. The closure as set forth in claim 9 and including:
 (a) said closure having a leading end relative to said forward advancement direction; and
 (b) said closure having a V-shaped set ring and an axially aligned point formed on said leading end to enhance setting engagement of said closure into a surface of a structural member.

12. The closure as set forth in claim 9 in combination with a bone implant screw adapted for connection to a bone fixation structural member, said bone implant screw including:
 (a) a threaded shank adapted for threaded implanting into a bone;
 (b) an open head having a pair of spaced apart arms having mutually facing channel surfaces defining a structural member receiving channel to receive a bone fixation structural member therebetween; and
 (c) each of said mutually facing channel surfaces having mating internal guide and advancement structure formed therein which are compatible with said flange of said closure to enable advancement of said closure into said channel to thereby clamp said bone fixation structural member when positioned therein.

13. The closure and bone implant screw combination as set forth in claim 12 wherein:
 (a) each of said guide and advancement structures of said bone implant screw include an outward anti-splay surface component which cooperates with said inward anti-splay surface component of said closure in such a manner as to resist a tendency of said arms to splay in reaction to torquing said closure into engagement with said fixation structural member.

14. The combination as set forth in claim 13 wherein:
 (a) said flange has a relatively enlarged outer periphery which forms said inward anti-splay surface component;
 (b) each of said guide and advancement structures are contoured in a complementary manner to said external thread to form said outward anti-splay surface component; and
 (c) said inward anti-splay surface component engages said outward anti-splay surface component when said closure is rotated into said open screw head of said bone implant screw.

15. A closure for setting engagement with a bone screw receiver and including a substantially cylindrical body having an outer cylindrical surface relative to a central closure axis and a substantially continuous guide and advancement flange extending helically about said outer cylindrical surface and having a forward advancement direction relative to said screw axis; said flange having a leading surface and a trailing surface relative to said forward advancement direction; said trailing surface being compound in contour and including an inward anti-splay surface component facing generally toward said closure axis and having a horizontal load surface between the anti-splay surface and the body; the trailing surface also having an outward raised portion with a top that is unloaded during usage; said leading surface sloping outwardly rearwardly from said body and being unloaded during usage; and said body having an axially aligned bore that opens onto a trailing surface of said body; said bore having a left handed helically wound thread that extends a plurality of revolutions around the bore sized and shaped to mate with a removal tool having a mating left handed thread.

16. The closure as set forth in claim 15 wherein said bore extends from said trailing surface of said body only partially through said body.

17. The closure as set forth in claim 15 and including:
 (a) an installation head that is shaped to enable non-slip engagement of said installation head by an installation tool; and
 (b) said installation head being connected to said closure by a breakaway region formed in such a manner that said breakaway region fails in response to a selected level of torque between said installation head and said closure to enable separation of said installation head from said closure.

18. The closure as set forth in claim 15 wherein:
 (a) said closure has a leading end relative to said forward advancement direction; and
 (b) said closure having a V-shaped set ring and a point formed on said forward end to enhance setting engagement of said closure into a surface of such a structural member.

19. The closure as set forth in claim 15 in combination with a bone screw adapted for connection to a bone fixation structural member, said bone implant screw including:
 (a) a threaded shank adapted for threaded implantation into a bone;
 (b) an open head formed by a pair of spaced apart arms having mutually facing channel surfaces defining a structural member receiving channel to receive a bone fixation structural member;
 (c) each of said mutually facing channel surfaces having respective mating guide and advancement structures formed therein which are compatible with said guide and advancement flange of said closure to enable guiding and advancement of said closure into said channel to thereby clamp said bone fixation structural member therein; and (d) said mating guide and advancement structures of said bone implant screw including an outward anti-splay surface component which cooperates with said inward anti-splay surface component of said closure in such a manner as to resist a tendency of said arms to splay in reaction to forces being applied thereto.

20. The closure and bone screw combination as set forth in claim 19 wherein:
 (a) said guide and advancement flange has a relatively enlarged outer periphery region which forms said inward anti-splay surface component;
 (b) said mating guide and advancement structures are contoured in a complementary manner to said guide and advancement flange to form said outward anti-splay surface component; and
 (c) said inward anti-splay surface component engages said outward anti-splay surface component when said closure is guided and advanced into said open screw head of said bone implant screw.

\* \* \* \* \*